United States Patent
Asano et al.

(10) Patent No.: US 8,566,995 B2
(45) Date of Patent: Oct. 29, 2013

(54) ENDOSCOPIC DUCT CLEANING TOOL

(75) Inventors: Hiroyuki Asano, Kanagawa (JP); Yasuo Yoshikawa, Kanagawa (JP); Yasuhiro Hoshino, Kanagawa (JP); Hirokazu Higuchi, Kyoto (JP); Takayuki Nitta, Kyoto (JP)

(73) Assignee: Piolax Medical Devices, Inc., Yokohama-Shi, Kanagawa (JP)

( * ) Notice: Subject to any disclaimer, the term of this patent is extended or adjusted under 35 U.S.C. 154(b) by 265 days.

(21) Appl. No.: 13/138,353

(22) PCT Filed: Feb. 12, 2010

(86) PCT No.: PCT/JP2010/052052
§ 371 (c)(1),
(2), (4) Date: Aug. 5, 2011

(87) PCT Pub. No.: WO2010/093008
PCT Pub. Date: Aug. 19, 2010

(65) Prior Publication Data
US 2011/0289705 A1 Dec. 1, 2011

(30) Foreign Application Priority Data
Feb. 12, 2009 (JP) ............................. P. 2009-029302

(51) Int. Cl.
*B08B 9/027* (2006.01)
(52) U.S. Cl.
USPC .................................... 15/104.16; 15/104.05
(58) Field of Classification Search
USPC .......................... 15/104.05, 104.16, 104.165, 15/104.17–104.19, 104.2
See application file for complete search history.

(56) References Cited

U.S. PATENT DOCUMENTS

| | | | |
|---|---|---|---|
| 5,297,310 A * | 3/1994 | Cox et al. | 15/106 |
| 6,045,623 A * | 4/2000 | Cannon | 134/8 |
| 6,699,331 B1 * | 3/2004 | Kritzler | 134/8 |
| 2003/0213074 A1 | 11/2003 | Kawazoe et al. | |

(Continued)

FOREIGN PATENT DOCUMENTS

| | | |
|---|---|---|
| JP | 60-72507 A | 4/1985 |
| JP | 7-194617 A | 8/1995 |
| JP | 8-187478 A | 7/1996 |
| JP | 10-272097 A | 10/1998 |
| JP | 3406081 B2 | 3/2003 |
| JP | 2003-190092 A | 7/2003 |

(Continued)

*Primary Examiner* — Mark Spisich
(74) *Attorney, Agent, or Firm* — McGinn IP Law Group, PLLC

(57) ABSTRACT

Provided is an endoscopic duct cleaning tool which uses elastic porous members to prevent the inside of a duct of an endoscope from being damaged, and which can firmly fix the elastic porous members to a core wire and secure a sufficient thickness in each of the elastic porous members.
This endoscopic duct cleaning tool 1 is inserted into a duct 53 of an endoscope 50 to clean the duct 53. The endoscopic duct device 1 includes a core wire 10 consisting of a stranded wire, plural cylindrical elastic porous members 20 disposed at certain intervals and at certain places in an axial direction of the core wire 10 so as to cover an outer circumference of the core wire 10 directly, and resin tubes 30 covering outer circumferences of portions of the core wire 10 which are not covered with the elastic porous members 20. An outer diameter of each of the resin tubes 30 is formed to be larger than an inner diameter of each of the elastic porous members 20. A frontmost end tube 31 and a basemost end tube 32 disposed in a frontmost end portion and a basemost end portion of the core wire 10 respectively are fixedly attached to the core wire 10.

6 Claims, 13 Drawing Sheets

(56) References Cited

U.S. PATENT DOCUMENTS

2006/0162105 A1* 7/2006 Abe .............................. 15/104.2
2010/0139018 A1* 6/2010 Maslanka ................... 15/104.05
2010/0163074 A1* 7/2010 Hansen ............................. 134/8

FOREIGN PATENT DOCUMENTS

| | | |
|---|---|---|
| JP | 2004-24842 A | 1/2004 |
| JP | 2004-113579 A | 4/2004 |
| JP | 2006-051057 A | 2/2006 |

* cited by examiner

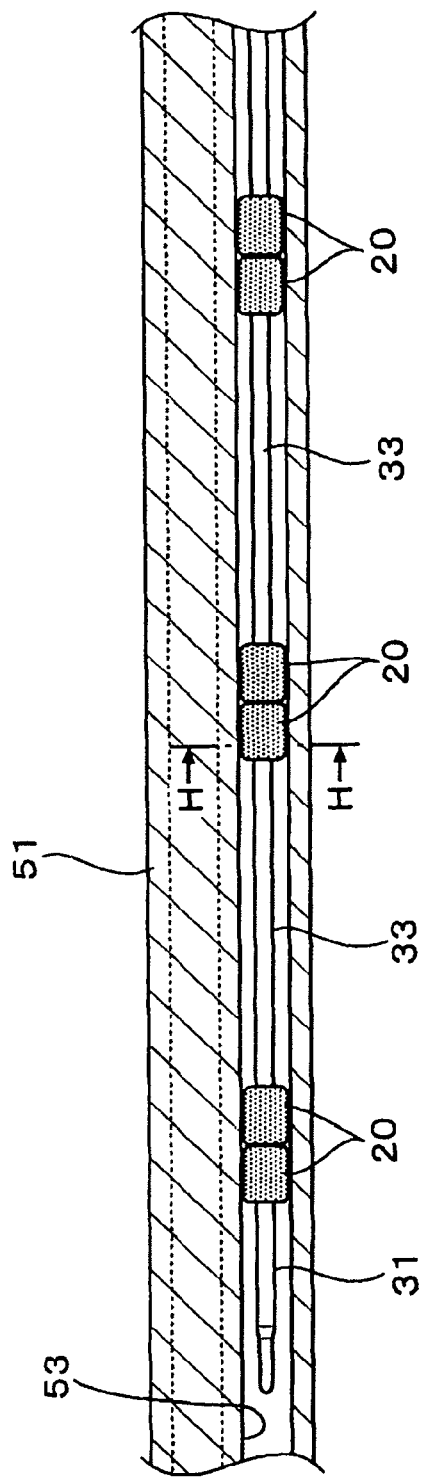
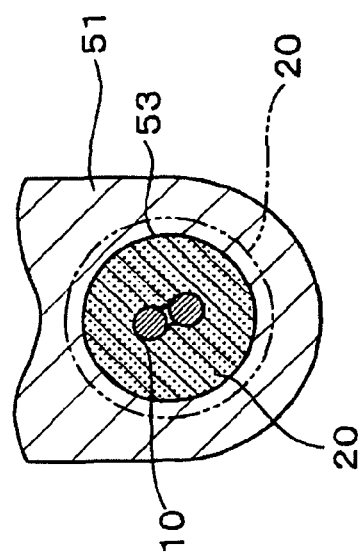

ENDOSCOPIC DUCT CLEANING TOOL

TECHNICAL FIELD

The present invention relates to an endoscopic duct cleaning tool which is inserted into a duct of an endoscope so as to clean the duct.

BACKGROUND ART

In the background art, endoscopes have been used for inspecting or treating the inside of the esophagus, the stomach, the duodenum, the small intestine, the large intestine, etc. An endoscope generally has a flexible insertion portion in which plural ducts (also called channels or lumens) are formed. An optical system such as a fiber scope is inserted into a duct and disposed therein. Thus, a place to be inspected is imaged by the optical system. For example, a tissue sampling tool, a guide wire, a catheter for administering a drug solution, etc. are inserted into the other ducts so as to sample a tissue from an affected area or treat the affected area.

When an endoscope is used, various matters such as blood, gastric juice, intestinal juice, undigested gastric contents, etc. may enter a duct of the endoscope and adhere to an inner wall of the duct to thereby cause dirt. From a hygienic viewpoint, it is necessary to clean such dirt thoroughly and keep the inside of the duct clean after termination of inspection with the endoscope.

As such cleaning tools to be used for cleaning the inside of an endoscopic duct, various structures have been proposed. For example, Patent Document 1 discloses a brush for cleaning a duct of an endoscope, in which brush portions are provided in plural places of a front end portion of a shaft.

Patent Document 2 discloses a cleaning assistant tool which includes a liquid non-absorbing elastic body having a continuous circumference with an outer diameter larger than an inner diameter of a duct in an endoscope, and a shaft member for supporting the elastic body. Patent Document 2 also discloses a duct moisture removing tool in which plural spherical water absorbing members are arranged in series and linked together at their centers by an operating wire.

Patent Document 3 discloses an endoscope cleaning brush which includes a long body portion having enough flexibility to bend along an inner wall of a duct of an endoscope when the body portion is inserted into the duct, a brush portion provided in the body portion, and a sponge portion provided in the body portion. A tube member is used as the body portion.

PRIOR TECHNICAL DOCUMENTS

Patent Documents
  Patent Document 1: JP-2004-113579-A
  Patent Document 2: JP-3406081-B
  Patent Document 3: JP-2006-051057-A

SUMMARY OF THE INVENTION

Problems that the Invention is to Solve

However, in Patent Document 1, the inside of the duct of the endoscope may be easily damaged easily because the brush consisting of a large number of fibers etc. rubs an inner wall of the duct for cleaning. When the inside of the duct is damaged, dirt may easily adhere to the damaged portions. The inside of the duct can be prevented from being damaged if the fibers etc. of the brush are made of a soft material or a force to press the brush into the duct is adjusted moderately. In that case, however, dirt cannot be removed thoroughly. Further, since foreign matters staying in the duct can slip through the brush, it is difficult to remove the foreign matters.

Patent Document 2 discloses the cleaning assistant tool in which the liquid non-absorbing elastic body is attached to the shaft member. The liquid non-absorbing elastic body is used for scraping out rinse water after the inside of a duct of an endoscope is cleaned with a brush. The non-absorbing elastic body alone cannot clean the inside of the duct. Although Patent Document 2 also discloses the duct moisture removing tool in which the plural spherical water absorbing members are arranged in series and linked together by the operating wire, in this case, the water absorbing members may be displaced with respect to the operating wire. Further, since the water absorbing members which are spherical cannot secure wide contact areas with an inner wall of the duct, a satisfactory cleaning effect may not be obtained.

Further, in Patent Document 3, dirt in a duct of an endoscope is scraped with the brush portion, held by the sponge portion, and discharged to the outside of the duct. However, similarly to Patent Document 1, since the inside of the duct is rubbed with the brush, the inside of the duct may be easily damaged. In addition, the sponge portion is attached to the body portion constituted by a tube member. Accordingly, when an outer diameter of the cleaning brush is limited for the sake of an inner diameter of the duct of the endoscope, a large thickness cannot be secured in the sponge portion due to an outer diameter of the tube member. Thus, a satisfactory elastic force may not be obtained.

An object of the present invention to provide an endoscopic duct cleaning tool which uses elastic porous members to prevent the inside of a duct of an endoscope from being damaged, and which can firmly fix the elastic porous members to a core wire and secure a sufficient thickness in each of the elastic porous members.

Means for Solving the Problems

A first invention provides an endoscopic duct cleaning tool which is inserted into a duct of an endoscope to clean the duct, including: a core wire which consists of a stranded wire; a plurality of cylindrical elastic porous members which are disposed at certain intervals and at certain places in an axial direction of the core wire so as to directly cover outer circumferences of the core wire; and resin tubes which cover outer circumferences of portions of the core wire which are not covered with the elastic porous members, wherein an outer diameter of each of the resin tubes is formed to be larger than an inner diameter of each of the elastic porous members, and wherein the resin tubes disposed in a frontmost end portion and a basemost end portion of the core wire are fixedly attached to the core wire.

According to the above invention, no brush is used but the elastic porous members are used to rub an inner circumference of the duct of the endoscope to clean the duct. Thus, an inner wall of the duct will not be damaged.

The elastic porous members are attached to the outer circumferences of the core wire so as to cover the outer circumferences of the core wire directly, and the outer circumferences of the portions of the core wire which are not covered with the elastic porous members are covered with the resin tubes. Thus, the resin tubes can prevent the elastic porous members from being displaced with respect to the core wire.

Since the elastic porous members are attached directly to the core wire, the thickness of each elastic porous member can be secured even if an outer diameter of the elastic porous member is limited in accordance with an inner diameter of the duct of the endoscope. Thus, a repulsive force generated when each elastic porous member is pressed and contracted onto the inner circumference of the duct is improved so that the elastic porous member can easily come into tight contact with the inner circumference of the duct to thereby clean the inner circumference of the duct efficiently.

The outer circumferences of the portions of the core wire which are not covered with the elastic porous members are covered with the resin tubes. Therefore, the core wire can be prevented from touching the inner circumference of the duct directly, so that the inner circumference of the duct can be prevented from being damaged.

Since the core wire consists of a stranded wire, flexibility of the core wire is not spoiled even when the core wire has an outer diameter large enough to be gripped easily. Thus, appropriate rigidity can be kept so that pushability can be kept.

A second invention provides, based on the first invention, the cleaning tool, wherein the elastic porous members are directly bonded to the core wire.

According to the above invention, the elastic porous members are attached directly to the core wire. Accordingly, the elastic porous members can be retained firmly in respective positions in a front end portion of the core wire without displacement.

A third invention provides, based on the first or second invention, the cleaning tool, wherein the elastic porous members are grouped into sets so that the sets of the elastic porous members are disposed in plurality at the certain intervals and at the certain places in the outer circumference of the core wire, each set including a plurality of the elastic porous members disposed adjacently to each other.

According to the above invention, when the duct cleaning tool is inserted into the duct and slid, sliding-direction-side edge portions of elastic porous members adjacent to each other are brought into highly tight contact with the inner circumference of the duct while being deformed in the sliding direction. Thus, dirt can be scraped effectively. Further, at that time, a gap appears between a base end portion of a sliding-direction-side elastic porous member and a front end portion of the adjacent elastic porous member. Therefore, dirt scraped in the gap can be captured so that the dirt can be discharged surely to the outside of the duct without staying therein.

A fourth invention provides, based on any one of the first to third inventions, the cleaning tool, wherein the resin tube disposed in a frontmost end portion of the core wire extends by a certain length from a frontmost end of the core wire.

According to the above invention, the core wire is not disposed in the frontmost end portion of the duct cleaning tool, but the frontmost end portion is constituted by the resin tube only, thereby improving flexibility and further preventing the inner circumference of the duct from being damaged.

A fifth invention provides, based on any one of the first to fourth inventions, the cleaning tool, wherein at least one kind of cuts, grooves and recesses is formed in an outer circumferential surface of each of the elastic porous members.

According to the above invention, at least one kind of cuts, grooves and recesses is formed in the outer circumferential surface of each of the elastic porous members. Accordingly, when the inside of the duct of the endoscope is cleaned, dirt can be captured in the open cuts, grooves or recesses so that the dirt can be more surely prevented from staying in the duct.

A sixth invention provides, based on the fifth invention, the cleaning tool, wherein the cuts are formed: to have a depth which extends from the outer circumferential surface of the elastic porous member but does not reach the core wire; to have an annular, spiral or arc shape extending in a circumferential direction of the elastic porous member; and to be arranged at certain intervals in the axial direction of the elastic porous member.

According to the above invention, the cuts are formed into annular, spiral or arc shapes extending in the circumferential direction of each of the elastic porous members and arranged at certain intervals in the axial direction of the elastic porous member. Accordingly, the number of edge portions coming in tight contact with the inner circumference of the duct to scrape dirt therefrom can be increased, and portions which can capture the dirt in the duct can be increased. Thus, the efficiency in cleaning the inside of the duct can be enhanced.

Effect of the Invention

According to the invention, elastic porous members attached to a core wire are used, and the core wire is covered with resin tubes and the elastic porous members. Accordingly, an inner wall of a duct can be cleaned without being damaged, and the resin tubes can prevent the elastic porous members from being displaced with respect to the core wire. Since each elastic porous member is attached directly to the core wire, the elastic porous member can be made thick enough to improve its repulsive force when the elastic porous member is pressed and contracted. Accordingly, the elastic porous member can be easily brought into tight contact with an inner circumference of the duct. Since the core wire consists of a stranded wire, flexibility of the core wire is not spoiled even if the core wire has an outer diameter large enough to be gripped easily. Thus, appropriate rigidity can be kept so that pushability can be kept.

BRIEF DESCRIPTION OF THE DRAWINGS

FIGS. 4A and 4B show a state where the endoscopic duct cleaning tool is in use, FIG. 4A being an enlarged sectional view of FIG. 3, FIG. 4B being an enlarged sectional view taken along line H-H of FIG. 4A.

Figure 11A:
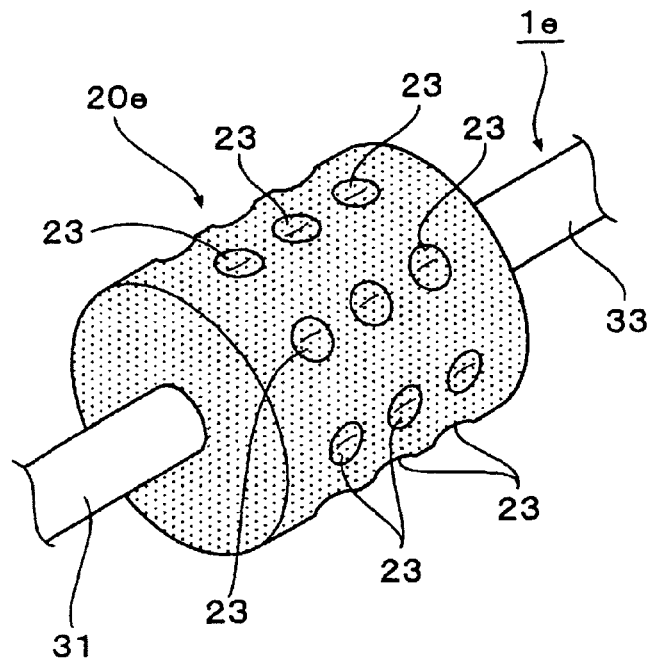
FIGS. 11A and 11B show a sixth embodiment of an endoscopic duct cleaning tool according to the invention, FIG.
Figure 11B:
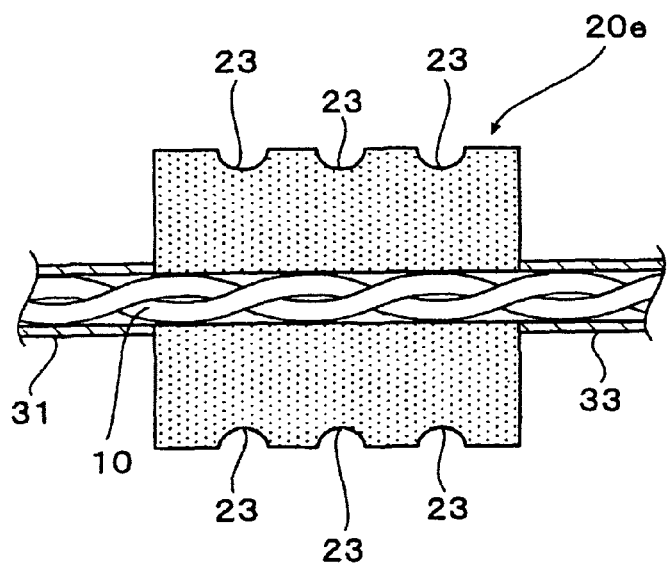

11A being an enlarged perspective view thereof, FIG. 11B being a sectional view thereof.

Figure 12A:
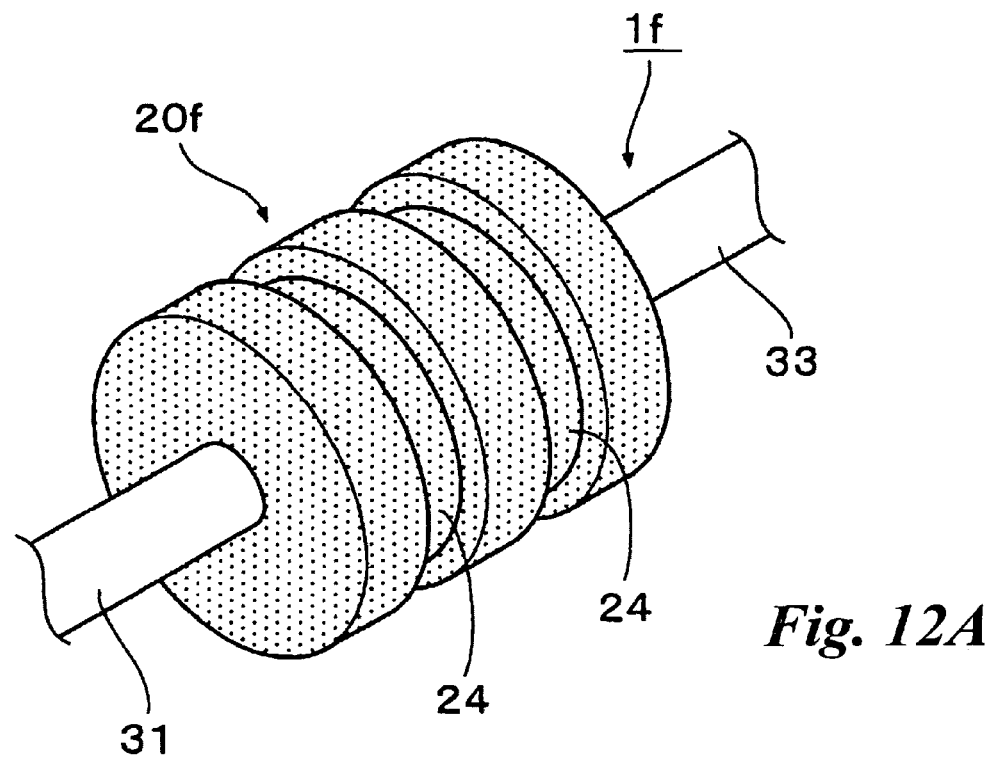
Figure 12B:
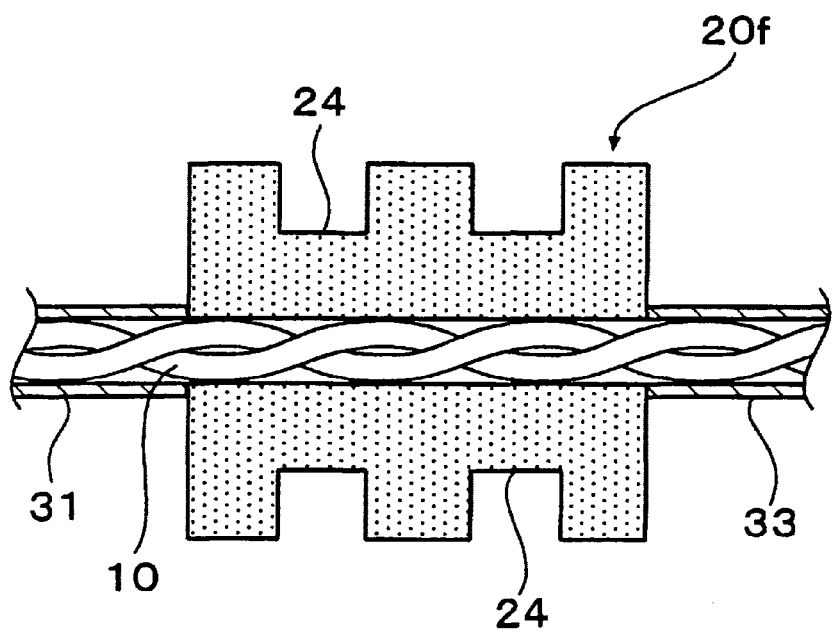

FIGS. 12A and 12B show a seventh embodiment of an endoscopic duct cleaning tool according to the invention, FIG. 12A being an enlarged perspective view thereof, FIG. 12B being a sectional view thereof.

Figure 13A:
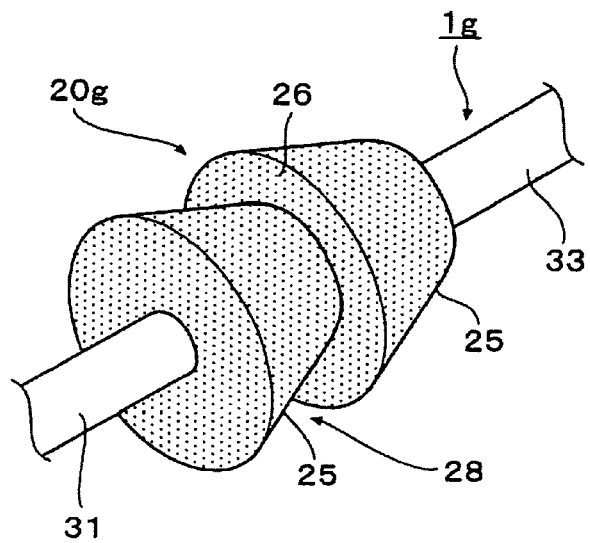
Figure 13B:
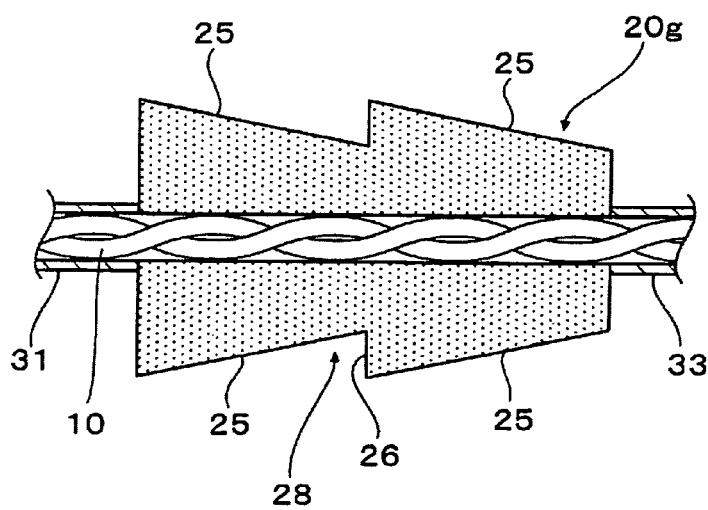

FIGS. 13A and 13B show an eighth embodiment of an endoscopic duct cleaning tool according to the invention, FIG. 13A being an enlarged perspective view thereof, FIG. 13B being a sectional view thereof.

MODE FOR CARRYING OUT THE INVENTION

A first embodiment of an endoscopic duct cleaning tool according to the invention will be described below with reference to the drawings.

Figure 3:
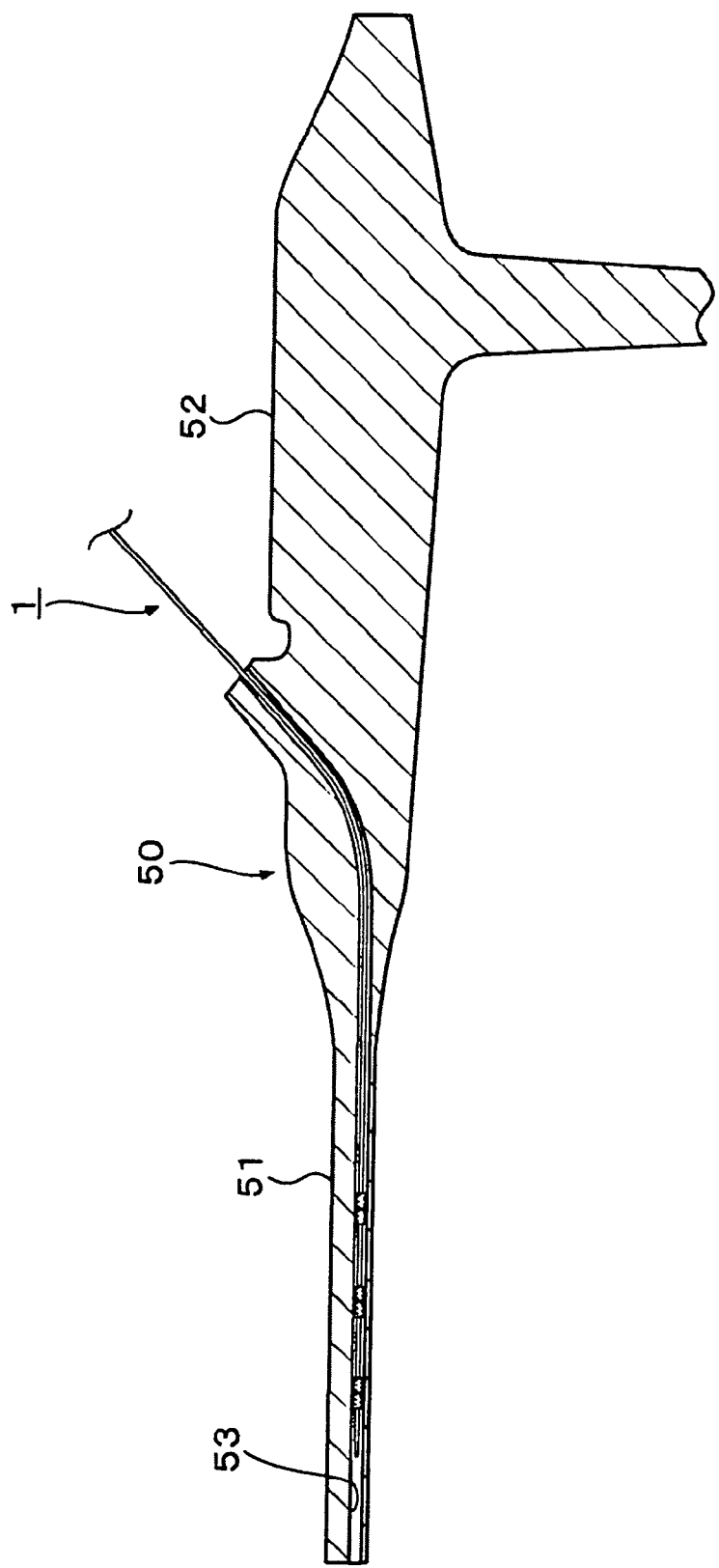
FIG. 3 shows a state where the endoscopic duct cleaning tool is inserted into a duct of an endoscope.

As shown in FIG. 3, this endoscopic duct cleaning tool (cleaning tool) 1 is inserted into a given duct 53 formed in an endoscope 50 so as to clean the duct 53. The endoscope 50 has an operating portion 52 and a flexible insertion portion 51 which is extended from the operating portion 52 and inserted into an esophagus, a stomach, a duodenum, a small intestine, a large intestine, a tubular organ such as a blood vessel, a urinary duct or a bile duct, or another body cavity of a human body. The duct 53 is formed to range from the operating portion 52 to a front end of the insertion portion 51.

Figure 1:
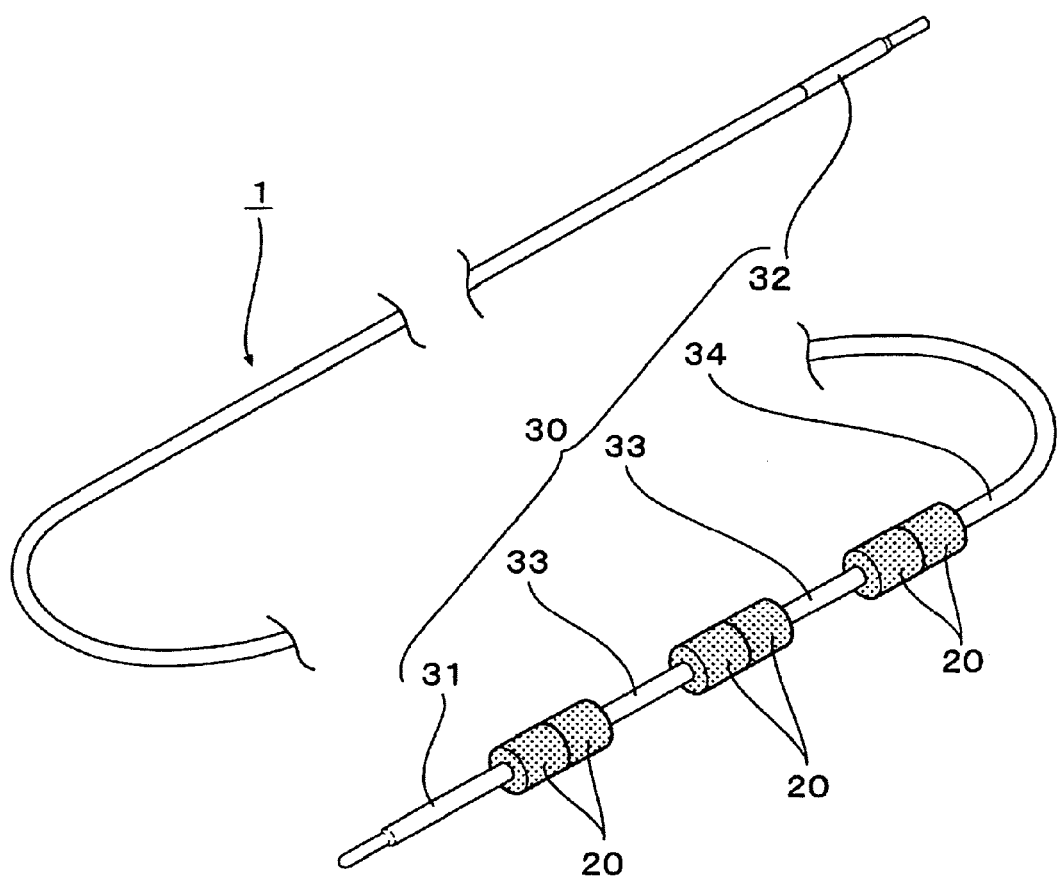
FIG. 1 is a perspective view showing a first embodiment of an endoscopic duct cleaning tool according to the invention.
Figure 2:
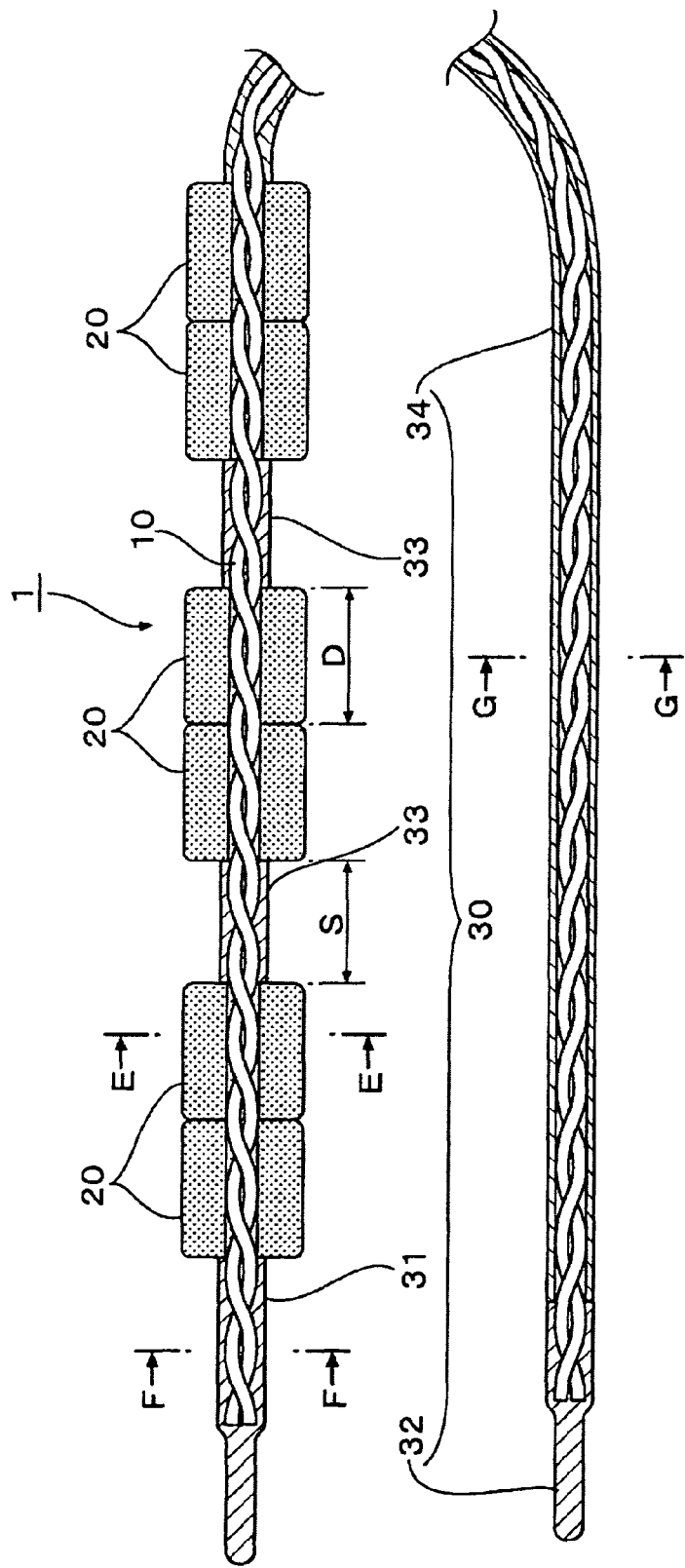
FIG. 2A is a longitudinally sectional view showing the endoscopic duct cleaning tool.
FIG. 2B is a sectional view taken along line E-E of FIG. 2A.
FIG. 2C is a sectional view taken along line F-F of FIG. 2A.
FIG. 2D is a sectional view taken along line G-G of FIG. 2A.

As shown in FIGS. 1 to 2D, the cleaning tool 1 according to the invention for cleaning the duct 53 of the endoscope 50 has a core wire 10 consisting of a stranded wire, plural cylindrical elastic porous members 20 disposed at certain intervals in a front end portion of the core wire 10 so as to cover an outer circumference of the core wire 10 directly, and resin tubes 30 covering outer circumferences of portions of the core wire 10 which are not covered with the elastic porous members 20.

As shown in FIGS. 2A to 2D, the core wire 10 is formed of a stranded wire which consists of a wire or plural wires stranded appropriately. As the material of the stranded wire, for example, stainless steel, Ni, W, piano wires, phosphor bronze, superelastic alloys such as Ni—Ti based superelastic alloys, Cu—Al—Ni based alloys or Cu—Zn—Al alloys, synthetic resin such as nylon or polyester, etc. may be used. Especially, stainless steel excellent in pushability is preferred. An outer diameter of the core wire 10 is not limited, but is preferably 0.5 to 3.0 mm, more preferably 1.5 to 2.5 mm from a view point of easiness to be gripped, operational performance of the cleaning tool 1, etc.

The elastic porous members 20 serving to clean the inside of the duct 53 of the endoscope 50 are disposed in the outer circumference of the front end portion of the core wire 10. In this embodiment, a pair of elastic porous members 20 and 20 each of which is formed into a cylindrical shape with a certain length are disposed adjacently to each other, and such pairs of elastic porous members 20 and 20 are disposed at certain intervals in three places of the front end portion of the core wire 10. That is, in this embodiment, three pairs of elastic porous members 20 and 20, that is, a total of six elastic porous members 20 are disposed in the front end portion of the core wire 10.

A porous material which has elasticity and includes infinitely many microscopic pores, such as sponge made of polyethylene foam, polyurethane foam or the like, chloroprene rubber sponge, natural rubber sponge, ethylene-propylene rubber sponge, nitrile rubber sponge, fluoro sponge, silicone sponge, etc. may be used preferably as the material of the elastic porous members 20. Preferably, elastic porous members whose density is 30 to 150 (kg/m$^3$) are used as the elastic porous members 20.

The elastic porous members 20 are disposed to cover the outer circumference of the front end portion of the core wire 10 directly without using any separately provided intercalated member such as a fixed tube or the like. In this cleaning tool 1, the elastic porous members 20 are prevented from being detached from the outer circumference of the core wire 10, by the resin tubes 30 which are disposed in a frontmost end portion and a basemost end portion of the core wire 10 respectively as will be described later. Thus, the elastic porous members 20 are attached directly to the outer circumference of the core wire 10 so that the elastic porous members 20 can be made thick. In addition, in this embodiment, a bonding agent is applied to an outer circumferential surface of the core wire 10 and/or inner circumferential surfaces of the elastic porous members 20. Thus, the elastic porous members 20 are bonded to the core wire 10 so as to enhance the fixing force further.

As shown in FIG. 2A, preferably a distance S between the pairs of elastic porous members 20 disposed in the front end portion of the core wire 10 (that is, a distance S between a base end side of a pair of elastic porous members 20 and 20 and a front end side of an adjacent pair of elastic porous members 20 and 20) is 5 to 20 mm. When the distance S is narrower than 5 mm, the range which can be cleaned at a time is reduced while the range in which the cleaning tool 1 can be moved along the duct 53 of the endoscope 50 is increased. Thus, the workability deteriorates. When the distance S is wider than 20 mm, the cleaning ranges of the elastic porous members 20 hardly overlap each other. Thus, the cleaning efficiency deteriorates.

Preferably, a length D of each elastic porous member 20 (see FIG. 2A) is 3 to 10 mm. When the length D of the elastic porous member 20 is shorter than 3 mm, a contact area of the elastic porous member 20 with an inner circumference of the duct 53 of the endoscope 50 is so small that the cleaning efficiency deteriorates. When the length D is longer than 10 mm, insertion resistance generated when the cleaning tool 1 is inserted into the duct 53 increases so that the operational performance of the cleaning tool 1 deteriorates.

Preferably, an outer diameter A of each elastic porous member 20 (see FIG. 2B) is formed to be larger than an inner diameter of the duct 53 of the endoscope 50. As a result, when the cleaning tool 1 is inserted into the duct 53 of the endoscope 50, each elastic porous member 20 is pressed by the inner circumference of the duct 53 so as to be contracted in diameter easily. Thus, a tight contact force of the elastic porous member 20 with the inner circumference of the duct 53 can be improved to enhance the cleaning efficiency.

In this case, preferably, the outer diameter A of each elastic porous member 20 is 1.05 to 1.25 times as large as the inner diameter of the duct 53. When the outer diameter A of the elastic porous member 20 is smaller than the aforementioned range, a contraction amount of the elastic porous member 20 which is generated when the cleaning tool 1 is inserted into the duct 53 of the endoscope 50 and the elastic porous member 20 is pressed by the inner circumference of the duct 53 is so small that the tight contact force of the elastic porous member 20 with the inner circumference of the duct 53 becomes insufficient. When the outer diameter A is larger than the aforementioned range, the contraction amount of the elastic porous member 20 is excessively large so as to result in increase in insertion resistance generated when the cleaning tool 1 is inserted into the duct 53. Thus, the operational performance of the cleaning tool 1 deteriorates.

Although a total of three pairs of elastic porous members 20 are disposed in this embodiment, plural sets of elastic porous members 20 may be disposed at certain intervals, each set including three or more elastic porous members 20 arranged adjacently to one another. Alternatively, elastic porous members 20 may be disposed separately at certain intervals. However, preferably, in order to enhance the cleaning effect, plural sets of elastic porous members 20 are disposed at certain intervals, each set including plural elastic porous members 20 arranged adjacently to one another, as will be described later.

Although a cylindrical shape is used as the shape of each elastic porous member 20 in this embodiment, the shape is not limited. For example, the shape may be a so-called potbellied shape which is cylindrical as a whole and swells in its axially intermediate portion and whose diameter is reduced gradually toward its axially opposite ends, a so-called double enveloping shape which is cylindrical likewise and sinks in its axially intermediate portion and whose diameter is expanded gradually toward its axially opposite ends, or the like.

The outer circumferences of portions of the core wire 10 which are not covered with the elastic porous members 20 are covered with the resin tubes 30. As shown in FIG. 2A, the resin tubes 30 in this embodiment include a frontmost end tube 31 disposed in a frontmost end portion of the core wire 10 in front of the frontmost-end-side elastic porous member 20, a basemost end tube 32 disposed in a basemost end portion of the core wire 10, inter-porous-member tubes 33 each disposed between the adjacent elastic porous members 20, and a user's side tube 34 disposed between the basemost-end-side elastic porous member 20 and the basemost end tube 32. Incidentally, the frontmost end tube 31 serves as a resin tube disposed in the frontmost end portion of the core wire in this invention, and the basemost end tube 32 serves as a resin tube disposed in the basemost end portion of the core wire in this invention.

In this embodiment, of the tubes belonging to the resin tubes 30, the user's side tube 34 is formed of synthetic resin such as nylon elastomer, polyethylene, polyurethane, polyether block amide, polyvinyl chloride, vinyl acetate, or fluoro resin. On the other hand, the frontmost end tube 31, the basemost end tube 32 and the inter-porous-member tubes 33 are formed of heat-shrinkable synthetic resin such as polyolefin, fluoro resin, or silicone rubber.

Thus, the frontmost end tube 31, the basemost end tube 32 and the inter-porous-member tubes 33 adhere to the outer circumference of the core wire 10 so as to be fixed thereto in respective positions, while the user's side tube 34 is disposed to cover the outer circumference of the core wire 10.

As shown in FIG. 2A, the frontmost end tube 31 disposed in the frontmost end portion of the core wire 10 extends by a certain length from the frontmost end of the core wire 10. Accordingly, when the frontmost end tube 31 whose diameter is expanded is placed in the frontmost end portion of the core wire 10 and heated, the base end side of the frontmost end tube 31 is reduced in diameter so as to adhere to the frontmost end portion of the core wire 10. At the same time, the frontmost end tube 31 is attached to extend from the front end of the core wire 10 so that a front end side portion of the frontmost end tube 31 where the core wire 10 is not disposed is reduced in diameter, compared with the portion of the frontmost end tube 31 adhering to the core wire 10.

In the same manner as the frontmost end tube 31, the basemost end tube 32 disposed in the basemost end portion of the core wire 10 also extends by a certain length from a rearmost end of the core wire 10. Accordingly, the basemost end tube 32 is attached so that a front end side of the basemost end tube 32 adheres to the basemost end portion of the core wire 10, while a base end side portion of the basemost end tube 32 in which the core wire 10 is not disposed is reduced in diameter, compared with the portion of the basemost end tube 32 adhering to the core wire 10.

FIG. 2C shows a sectional view of a tube (the frontmost end tube 31 here) made of heat-shrinkable synthetic resin, and FIG. 2D shows a sectional view of the user's side tube 34 made from synthetic resin which is not heat-shrinkable. As shown in FIGS. 2C and 2D, an outer diameter B of each tube is formed to be larger than an inner diameter a of each of the elastic porous members 20.

As described above, in this cleaning tool 1, the portions of the core wire 10 which are not covered with the elastic porous members 20 are covered with the resin tubes 30, while the outer diameter B of each tube belonging to the resin tubes 30 is larger than the inner diameter a of each of the elastic porous members 20, and of the resin tubes 30, the frontmost end tube 31 and the basemost end tube 32 disposed in the frontmost end portion and the basemost end portion of the core wire 10 respectively are fixedly attached to the core wire 10. As a result, the elastic porous members 20 can be prevented from being detached from the core wire 10, and displacements of the elastic porous members 20 in the axial direction of the core wire 10 can be restricted surely. In addition, in this embodiment, each of the inter-porous-member tubes 33 disposed between the adjacent elastic porous members 20 is fixedly attached to the outer circumference of the core wire 10. Accordingly, displacements of the elastic porous members 20 can be restricted more surely.

Further, in this embodiment, since the elastic porous members 20 are bonded to the outer circumference of the core wire 10 directly through a bonding agent or the like, the elastic porous members 20 can be more firmly retained in respective positions in the front end portion of the core wire 10 without any displacement.

Next, description will be made on how to use the thus configured cleaning tool 1 according to the present invention. That is, the user's side tube 34 is gripped so that a user's side of the core wire 10 is gripped, and the front end portion of the cleaning tool 1 is plugged into an insertion entrance hole (an opening on the operating portion 52 side) or an insertion exit hole (an opening on the front end side of the insertion portion 51) of the duct 53 which is formed in the endoscope 50 shown in FIG. 3 so that the front end portion of the cleaning tool 1 is inserted into the duct 53.

Figure 5:
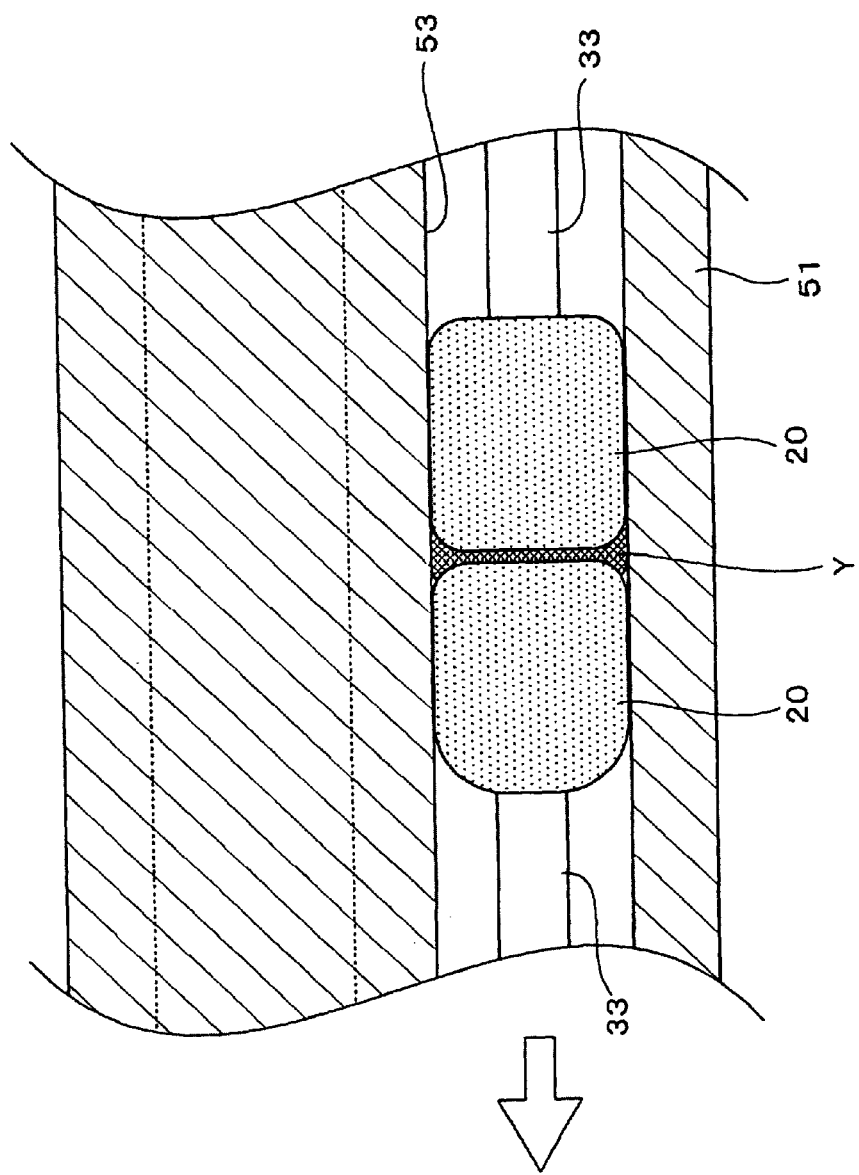
FIG. 5 is an enlarged sectional view of FIG. 4A, showing the state where the endoscopic duct cleaning tool is in use.

Then, as shown in FIG. 4B, each elastic porous member 20 is pressed by the inner circumference of the duct 53 so as to be reduced in diameter (the imaginary line in FIG. 4B designates the original outer diameter of the elastic porous member 20). Due to the repulsive force, the elastic porous member 20 is brought into tight contact with the inner circumference of the duct 53. When the core wire 10 is slid appropriately in this state, the elastic porous members 20 disposed in the front end portion of the core wire 10 scrape dirt adhering to the inner circumference of the duct 53 while sliding on the inner circumference of the duct 53, as shown in FIGS. 4A and 5. Thus, the inside of the duct 53 can be cleaned efficiently.

On this occasion, in the cleaning tool 1 according to the present invention, not a brush but the elastic porous members 20 which are comparatively soft slide on the inner circumference of the duct 53 to scrape dirt therefrom. Thus, the inner circumference of the duct 53 can be prevented from being damaged. Since the portions of the core wire 10 which are not covered with the elastic porous members 20 are covered with the resin tubes 30 including the frontmost end tube 31, the basemost end tube 32, the inter-porous-member tubes 33 and the user's side tube 34 so that the outer circumference of the core wire 10 is entirely covered, the inner circumference of the duct 53 can be prevented from being damaged.

Since the core wire 10 consists of a stranded wire. Accordingly, flexibility is not spoiled even if the core wire 10 has an outer diameter large enough to be gripped easily. Thus, appropriate rigidity can be kept to keep pushability, so that the core wire 10 can be slid smoothly without damaging the inner circumference of the duct 53, and the operational performance of the cleaning tool 1 can be improved.

In this cleaning tool 1, the elastic porous members 20 are disposed to cover the outer circumference of the front end portion of the core wire 10 directly so that the elastic porous members 20 can be formed to be thick. Accordingly, when the cleaning tool 1 is inserted into the duct 53 of the endoscope 50, the repulsive force which is generated when each elastic porous member 20 is pressed and contracted by the inner circumference of the duct 53 is improved so that the elastic porous member 20 can be brought into tight contact with the inner circumference of the duct 53 easily. Thus, the inner circumference of the duct 53 can be cleaned more efficiently.

Since the core wire 10 consists of a stranded wire, the inner circumferential portion of each elastic porous member 20 is elastically deformed to bite between wires twisted as the stranded wire when the elastic porous member 20 is inserted into the duct 53 and pressed and contracted by the inner circumference of the duct 53, as shown in FIG. 4B. Accordingly, the elastic porous member 20 can be firmly retained and fixed in a certain position in the front end portion of the core wire 10, and displacement of the elastic porous member 20 can be restricted more surely.

In this embodiment, as shown in FIGS. 2A to 2D, three pairs of elastic porous members 20 are disposed at certain intervals and at three places on the outer circumference of the front end portion of the core wire 10. Accordingly, when the front end portion of the cleaning tool 1 is inserted into the duct 53 and slid, sliding-direction-side edge portions of the elastic porous members 20 and 20 adjacent to each other are deformed in the sliding direction and brought into highly tight contact with the inner circumference of the duct 53, as shown in FIG. 5. Thus, dirt can be scraped effectively. In addition, on that occasion, there appears a gap between the base end portion of the sliding-direction-side elastic porous member 20 and the front end portion of the elastic porous member 20 adjacent to the sliding-direction-side elastic porous member 20. Thus, scraped dirt Y can be captured in this gap, and the dirt Y can be discharged surely to the outside of the duct 53 without staying in the duct 53.

In the same manner, foreign matters or the like staying in the duct 53 are also pushed out by the elastic porous members 20. Thus, the foreign matters will not stay in the duct 53.

In this embodiment, as shown in FIG. 2A, the frontmost end tube 31 disposed in the frontmost end portion of the core wire 10 extends by a certain length from the frontmost end of the core wire 10. The core wire 10 is not disposed in the frontmost end portion of the cleaning tool 1, but only the frontmost end tube 31 is present there. Accordingly, flexibility can be improved, and the inner circumference of the duct 53 can be further prevented from being damaged.

The following method may be used as the method for using the cleaning tool 1. That is, the duct 53 may be cleaned such that the base end portion of the cleaning tool 1 in which no elastic porous member 20 is disposed is inserted and pushed into the duct 53 of the endoscope 50 while the base end portion of the cleaning tool 1 is pulled out from the opposite opening portion of the duct 53 to the insertion side.

Figure 6:
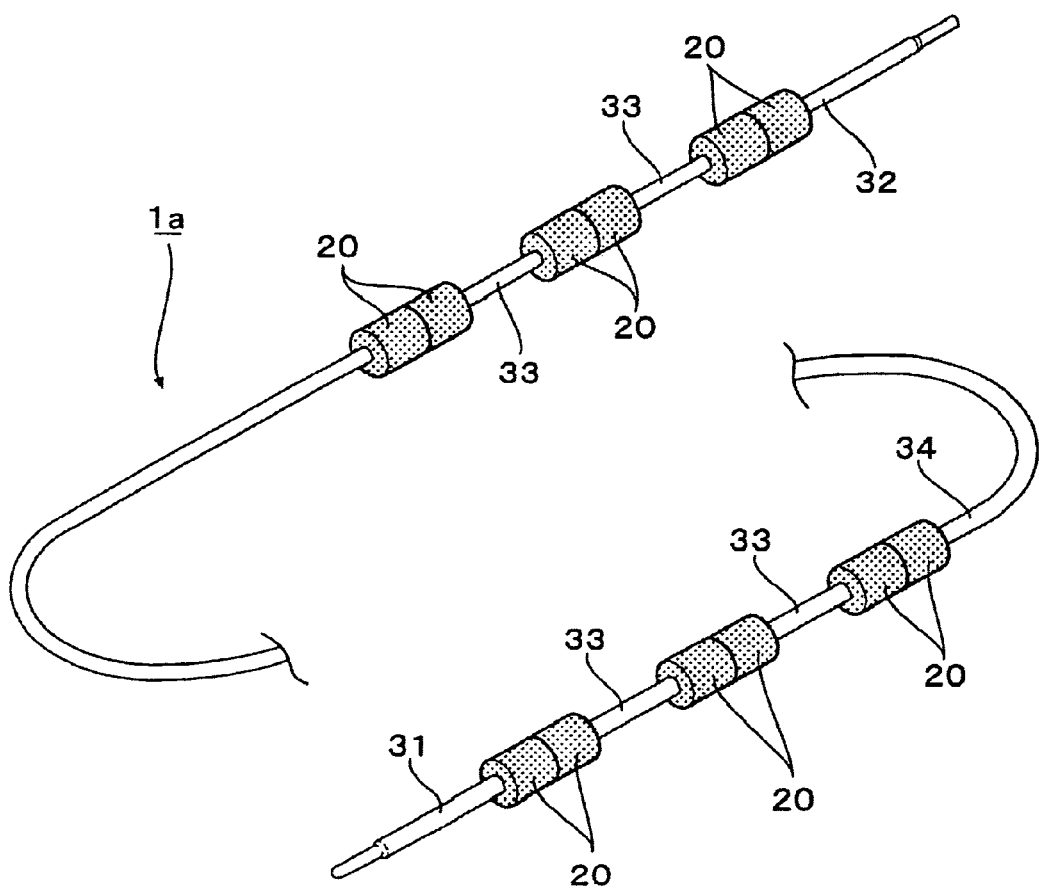
FIG. 6 is a perspective view showing a second embodiment of an endoscopic duct cleaning tool according to the invention.

FIG. 6 shows a second embodiment of an endoscopic duct cleaning tool in the present invention. Parts substantially identical to those in the aforementioned embodiments are referred to by the same numerals correspondingly, and description thereof will be omitted.

In an endoscopic duct cleaning tool (cleaning tool) 1a in this embodiment, three pairs of elastic porous members 20 and 20 are disposed in the outer circumference on the front end portion side of the core wire 10 in the same manner as in the endoscopic duct cleaning tool 1 in the previous embodiment. In addition, three pairs of elastic porous members 20 and 20 are also disposed in the outer circumference on the base end portion side of the core wire 10. Incidentally, the number of pairs of elastic porous members 20 and 20 to be disposed may be changed suitably, and a certain number of pairs of elastic porous members 20 and 20 may be provided at certain intervals. A certain number of pairs of elastic porous members 20 and 20 may be also disposed in the central portion of the sore wire 10.

In the duct cleaning tool 1a of FIG. 6, the elastic porous members 20 are disposed in the front end portion and the base end portion of the core wire 10. Accordingly, the inner circumference of the duct 53 is cleaned by the elastic porous members 20 which are first inserted into the duct 53, for example, by the elastic porous members 20 on the front end portion side (main cleaning). After that, the inner circumference of the duct 53 is cleaned without cleaning unevenness or not-cleaned areas by the elastic porous members 20 which are then inserted into the duct 53, for example, by the elastic porous members 20 on the base end portion side (finishing cleaning). In this manner, in the cleaning tool 1a according to this embodiment, main cleaning and finishing cleaning of the duct 53 can be performed at a time, and the cleaning efficiency can be enhanced.

Although plural pairs of elastic porous members 20 and 20 are disposed in the outer circumferences of the front end portion and the base end portion of the core wire 10 in the first or second embodiment, plural sets of elastic porous members 20 may be disposed at certain intervals, each set including three or more elastic porous members 20 disposed adjacently to one another. The number of combined elastic porous members 20 in each set or the number of those disposed sets is not limited.

Figure 7:
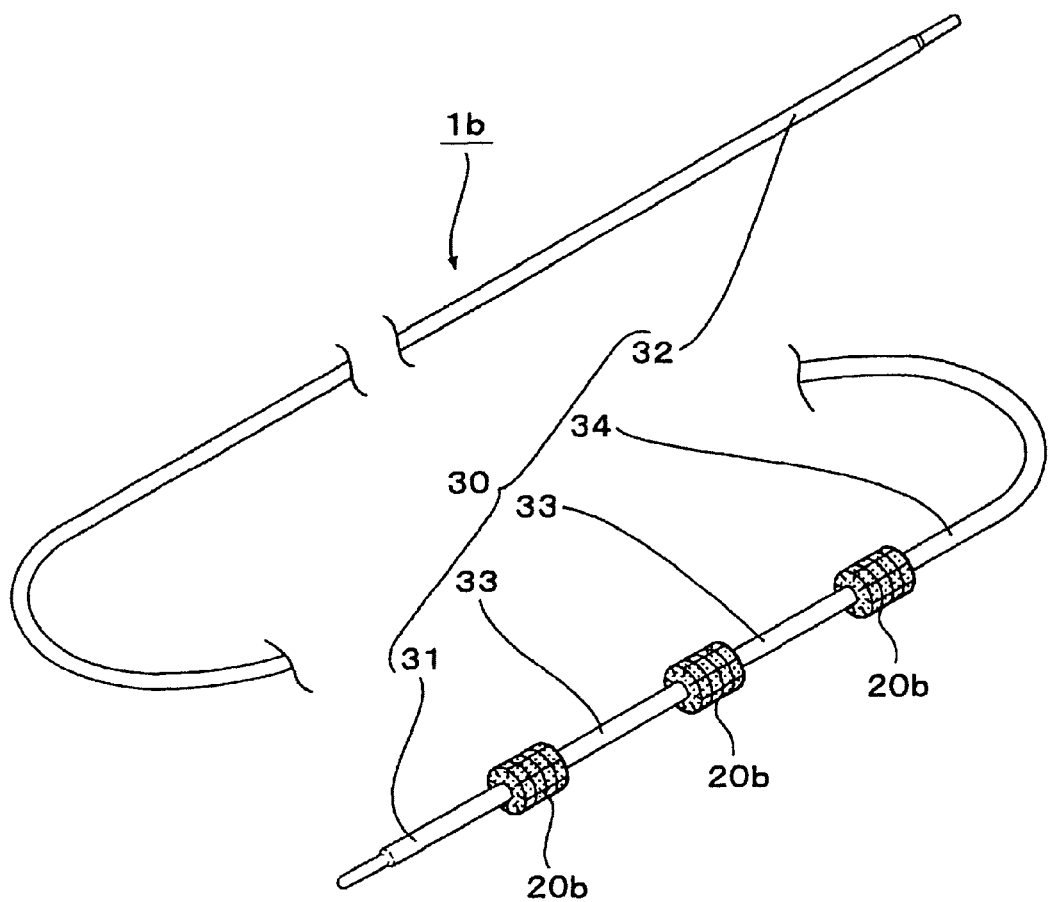
FIG. 7 is a perspective view showing a third embodiment of an endoscopic duct cleaning tool according to the invention.
Figure 8A:
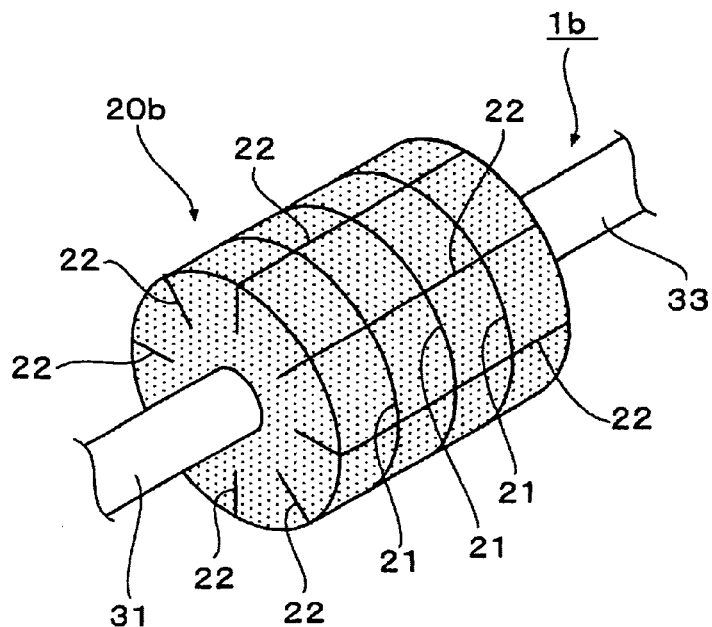
FIG. 8A is an enlarged perspective view of the endoscopic duct cleaning tool.
Figure 8B:
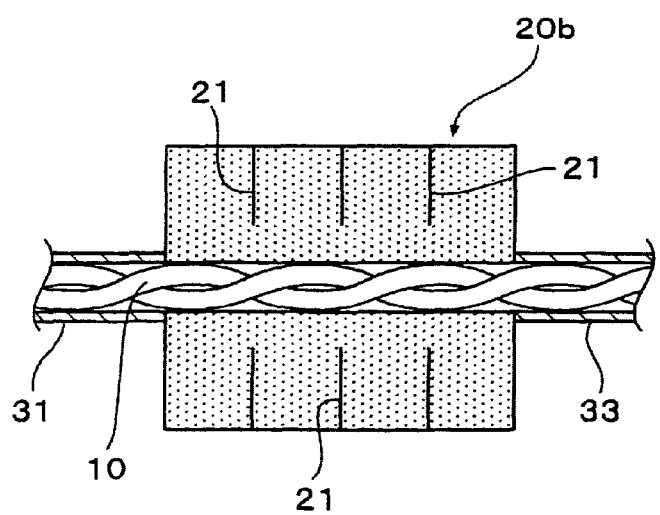
FIG. 8B is a sectional view thereof.

FIGS. 7 to 8B show a third embodiment of an endoscopic duct cleaning tool in the present invention. Parts substantially identical to those in the aforementioned embodiments are referred to by the same numerals correspondingly, and description thereof will be omitted.

In an endoscopic duct cleaning tool (cleaning tool) 1b in this embodiment, elastic porous members 20b are disposed separately at certain intervals and in three places in the front end portion of the core wire 10, differently from the first or second embodiment in which three pairs of elastic porous members 20 are disposed.

In the outer circumferences of the portions of the core wire 10 which are not covered with the elastic porous members 20b, a frontmost end tube 31 is disposed in front of the frontmost-end-side elastic porous member 20b, a basemost end tube 32 is disposed in the basemost end portion, each inter-porous-member tube 33 is disposed between the adjacent elastic porous members 20b, and a user's side tube 34 is disposed between the base-end-side elastic porous member 20b and the basemost end tube 32 in the same manner as in the first or second embodiment.

Plural cuts 21 each having a depth which extends from the outer circumferential surface of each elastic porous member 20b but does not reach the core wire 10 as shown in FIG. 8B are formed to extend in the circumferential direction of the elastic porous member 20b and to be arranged at certain intervals in the axial direction of the elastic porous member 20b, as shown in FIG. 8A. Likewise plural cuts 22 which do not reach the core wire 10 are formed to extend in the axial direction of the elastic porous member 20b and to be arranged at certain intervals in the circumferential direction of the elastic porous member 20b. In this manner, three circumferential cuts 21 and eight axial cuts 22 are formed in the outer circumferential surface of the elastic porous member 20b in this embodiment. In addition, each cut 21 in this embodiment has an annular shape formed all over the outer circumference of the elastic porous member 20b. Incidentally, each cut does not have to be annular, but may have an arc shape formed in the circumferential direction of the elastic porous member 20b.

Also in this embodiment, when the cleaning tool 1b is plugged into the duct 53 of the endoscope 50 and slid appropriately, each elastic porous member 20b slides on the inner circumference of the duct 53 to scrape adhering dirt therefrom in the same manner as in the aforementioned embodiments. Thus, the inside of the duct 53 can be cleaned.

On this occasion, the sliding-direction-side edge portion (sliding-direction-side circumferential angular portion) of the elastic porous member 20b is deformed in the sliding direction in accordance with the sliding operation of the cleaning tool 1b. Thus, the sliding-direction-side edge portion of the elastic porous member 20b is brought into highly tight contact with the inner circumference of the duct 53 so as to serve as a portion for scraping the dirt.

In this embodiment, the circumferential cuts 21 are formed axially in the elastic porous members 20b so that the number of edge portions for scraping dirt can be increased. The cuts 21 are normally closed, and opened to capture the dirt internally when the edge portions are deformed in the sliding direction. Thus, the dirt can be prevented from staying in the duct 53.

In this manner, the circumferential cuts 21 are formed axially in the elastic porous members 20b so that the number of edge portions coming into tight contact with the inner circumference of the duct 53 to scrape dirt therefrom can be increased, and the portions for capturing the dirt in the duct 53 can be increased. Thus, the cleaning efficiency in the duct 53 can be enhanced.

In addition to provision of the circumferential cuts 21, the axial cuts 22 are formed in the elastic porous members 20b so that flexibility of the elastic porous members 20b can be improved. Thus, insertion resistance generated when the cleaning tool 1b is inserted into the duct 53 is reduced, thereby improving the workability to clean the inside of the duct 53.

Figure 9A:
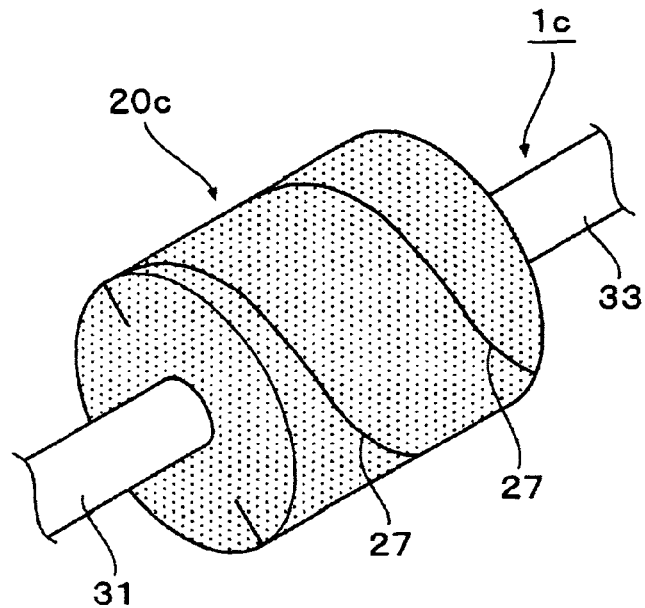
FIGS. 9A and 9B show a fourth embodiment of an endoscopic duct cleaning tool according to the invention, FIG. 9A being an enlarged perspective view thereof, FIG. 9B being a side view thereof.
Figure 9B:
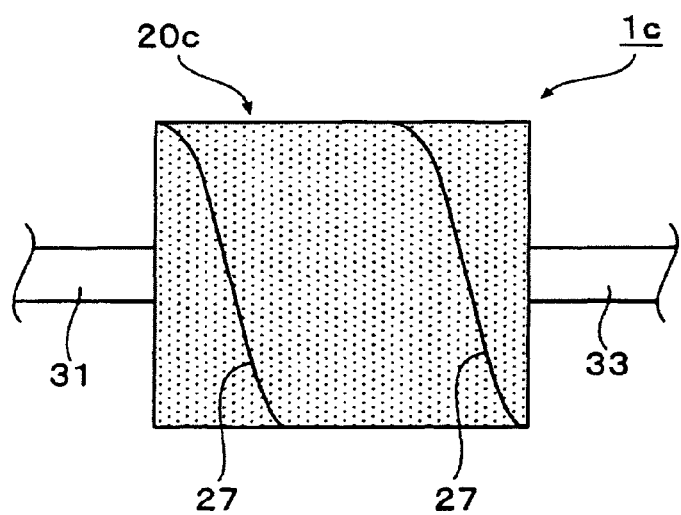

FIGS. 9A and 9B show a fourth embodiment of an endoscopic duct cleaning tool in the present invention. Parts substantially identical to those in the aforementioned embodiments are referred to by the same numerals correspondingly, and description thereof will be omitted.

In an endoscopic duct cleaning tool (cleaning tool) 1c in this embodiment, the shapes of cuts are different from those in the aforementioned third embodiment.

That is, as shown in FIGS. 9A and 9B, in the elastic porous member 20c in the embodiment, a cut 27 having a depth which extends from the outer circumferential surface of each elastic porous member 20c but does not reach the core wire 10 is formed spirally at a certain pitch in the axial direction of the elastic porous member 20c. That is, the spiral cut 27 running in the circumferential direction of each elastic porous member 20c is formed to be arranged at a certain interval in the axial direction of the elastic porous member 20c. The cut 27 in this embodiment is formed to extend spirally obliquely from the front end of the elastic porous member 20c (the left side in FIG. 9B) toward the base end (the right side in FIG. 9B) and not intermittently but continuously in the outer circumference of the elastic porous member 20c. Incidentally, the spiral cut 27 may include segmented portions on the way.

Since the spiral cuts 27 are formed axially in the elastic porous members 20c in this manner, the number of edge portions coming into tight contact with the inner circumference of the duct 53 to scrape dirt therefrom can be increased to enhance the cleaning efficiency in the duct 53. In addition, each elastic porous member 20c is slightly cut axially by the spiral cut 27 which is oblique with respect to the axial center of the elastic porous member 20c, thereby improving flexibility of the elastic porous member 20c and reducing insertion resistance into the duct 53.

Figure 10A:
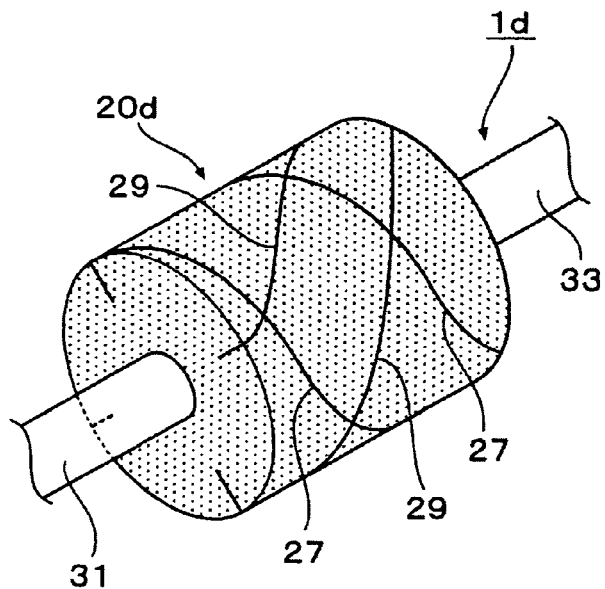
FIGS. 10A and 10B show a fifth embodiment of an endoscopic duct cleaning tool according to the invention, FIG. 10A being an enlarged perspective view thereof, FIG. 10B being a side view thereof.
Figure 10B:
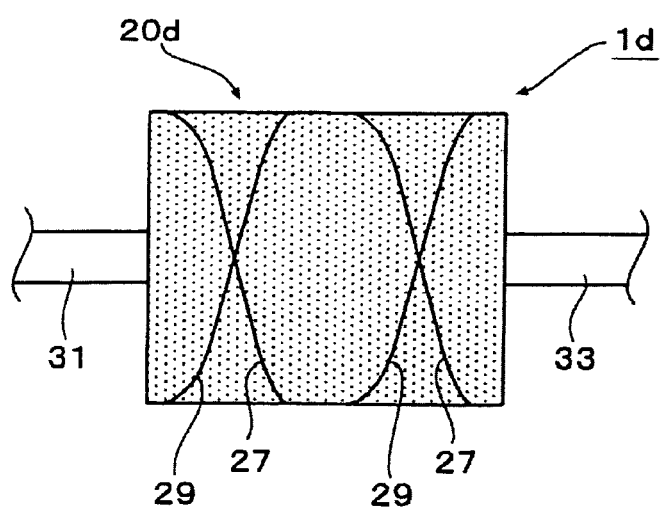

FIGS. 10A and 10B show a fifth embodiment of an endoscopic duct cleaning tool in the present invention. Parts substantially identical to those in the aforementioned embodiments are referred to by the same numerals correspondingly, and description thereof will be omitted.

In an endoscopic duct cleaning tool (cleaning tool) 1d in this embodiment, another spiral cut is additionally formed in the aforementioned fourth embodiment.

That is, as shown in FIGS. 10A and 10B, each elastic porous member 20d in this embodiment has a structure in which, in addition to the spiral cut 27 the same as that in the fourth embodiment, another cut 29 which extends in an opposite inclination direction to that of the cut 27, that is, which extends obliquely from the base end of the elastic porous member 20d toward the front end thereof is formed spirally at a certain pitch in the axial direction of the elastic porous member 20d. Thus, the two spiral cuts 27 and 29 are formed to cross each other.

According to this embodiment, the two spiral cuts 27 and 29 are formed in the elastic porous members 20d, so that the number of edge portions coming into tight contact with the inner circumference of the duct 53 to scrape dirt therefrom can be more increased to further enhance the cleaning efficiency in the duct 53. In addition, due to the two cuts 27 and 29, flexibility of each elastic porous member 20d can be more improved so that insertion resistance into the duct 53 can be further reduced.

FIGS. 11A and 11B show a sixth embodiment of an endoscopic duct cleaning tool in the present invention. Parts substantially identical to those in the aforementioned embodiments are referred to by the same numerals correspondingly, and description thereof will be omitted.

In an endoscopic duct cleaning tool (cleaning tool) 1e in this embodiment, the shape of each elastic porous member is different from those in the aforementioned third to fifth embodiments.

That is, as shown in FIGS. 11A and 11B, recesses 23 are formed in the outer circumferential surface of each elastic porous member 20e in this embodiment. In this embodiment, plural recesses 23 are formed at certain intervals in the axial direction of each elastic porous member 20e, and those recesses 23 disposed axially are further arranged at certain intervals in the circumferential direction of the elastic porous member 20e. In addition, the inner surface of each recess 23 has a rounded shape like an arc (see FIG. 11B). Incidentally, the recesses 23 may be placed in various arrangements such as staggered arrangement.

According to this embodiment, when the cleaning tool 1e is inserted into the duct 53 of the endoscope 50 in order to clean the inside of the duct 53, the contact area of each elastic porous member 20e with the inside of the duct 53 can be reduced due to the recesses 23 formed in the outer circumferential surface of the elastic porous member 20e. Thus, insertion resistance of the cleaning tool 1e can be reduced to improve the workability thereof. In addition, dirt can be captured in the recesses 23. Thus, the dirt can be prevented from staying in the duct 53. Further, plural recesses 23 are formed in the axial direction of each elastic porous member 20e. Therefore, even if a recess 23 in a certain position fails in capturing dirt and allows the dirt to stay behind, another recess 23 located axially on the base end side can capture the dirt. Thus, the amount of dirt staying behind can be reduced.

FIGS. 12A and 12B show a seventh embodiment of an endoscopic duct cleaning tool in the present invention. Parts substantially identical to those in the aforementioned embodiments are referred to by the same numerals correspondingly, and description thereof will be omitted.

In an endoscopic duct cleaning tool (cleaning tool) 1f in this embodiment, the shape of each elastic porous member is different from those in the aforementioned third to fifth embodiments.

That is, as shown in FIGS. 12A and 12B, annular grooves 24 are formed with certain widths in the outer circumferential surface of each elastic porous member 20f in this embodiment so as to extend in the circumferential direction of the elastic porous member 20f. The annular grooves 24 are formed at certain intervals in the axial direction of each elastic porous member 20f. In this embodiment, two circumferential annular grooves 24 are formed axially in the outer circumferential surface of each elastic porous member 20f.

According to this embodiment, the contact area of each elastic porous member 20f with the inside of the duct 53 of the endoscope 50 can be reduced due to the annular grooves 24. Thus, insertion resistance of the cleaning tool 1f can be reduced to improve the workability thereof. In addition, dirt can be captured in the annular grooves 24. Thus, the dirt can be prevented from staying in the duct 53. Moreover, since the annular grooves 24 are provided to extend circumferentially, the number of edge portions for scraping dirt can be increased to improve the cleaning efficiency.

FIGS. 13A and 13B show an eighth embodiment of an endoscopic duct cleaning tool in the present invention. Parts substantially identical to those in the aforementioned embodiments are referred to by the same numerals correspondingly, and description thereof will be omitted.

In an endoscopic duct cleaning tool (cleaning tool) 1g in this embodiment, the shape of each elastic porous member is different from that in the aforementioned fifth embodiment.

That is, as shown in FIGS. 13A and 13B, each elastic porous member 20g in this embodiment has a cylindrical shape in which plural tapered faces 25 each having a diameter expanded on the sliding direction side (see an arrow of FIG. 13B) and gradually narrowed on the opposite side to the sliding direction are formed axially. In this embodiment, two tapered faces 25 are formed continuously axially in the outer circumference of each elastic porous member 20g. The tapered face 25 and the tapered face 25 are connected through an end face 26 lying at right angles with respect to the axial center of the core wire 10. A recess 28 is formed between the sliding-direction-side tapered face 25 and the end face 26 in the outer circumferential surface of the elastic porous member 20g. This recess 28 has a bottom face whose diameter is reduced gradually from the sliding direction side toward the opposite side to the sliding direction.

According to this embodiment, the recess 28 having a bottom face whose diameter is reduced gradually from the sliding direction side toward the opposite side to the sliding direction is formed in the outer circumferential surface of each elastic porous member 20g, so that the contact area of the elastic porous member 20g with the inside of the duct 53 of the endoscope 50 can be reduced on a large scale. Thus, insertion resistance of the cleaning tool 1g can be reduced efficiently to improve the workability. In addition, dirt can be captured in the recess portion 28 so that the dirt can be prevented from staying in the duct 53. Further, due to the edge portion whose diameter is increased on the sliding direction side, the dirt in the duct 53 can be scraped, while the number of edge portions can be increased due to the recess 28 provided thus, thereby improving the cleaning efficiency.

Although only one elastic porous member is disposed in the axial direction of the core wire 10 as each elastic porous member 20b, 20c, 20d, 20e, 20f, 20g in each of the aforementioned third to eighth embodiments, two or more elastic porous members may be disposed adjacently to each other in the same manner as in the first or second embodiment. In this case, in the same manner as in the aforementioned first embodiment, dirt which cannot be captured by the cuts 21, the recesses 23 or 28 or the grooves 24 of each elastic porous member can be captured by a gap between the elastic porous member and another elastic porous member adjacent thereto (see FIG. 5). Thus, the dirt can be more surely prevented from staying behind.

Three or more elastic porous members may be made adjacent to one another and regarded as one set, and such sets may be disposed at certain intervals. The number of combined elastic porous members in each set or the number of those disposed sets is not limited.

Although one kind of cuts, grooves and recesses is formed in the outer circumferential surface of each elastic porous member in each of the aforementioned embodiments, two or more kinds of these cuts, grooves and recesses may be combined. For example, circumferential cuts 21 and axial cuts 22 in the third embodiment of FIGS. 7 to 8B or the like may be formed in addition to the recesses 23 in the sixth embodiment of FIGS. 11A and 11B. The combination of cuts, grooves and recesses or the number of disposed cuts, grooves and recesses is not limited.

EXAMPLE

The difference between the amount of dirt staying behind in a duct when an endoscopic duct cleaning tool according to the present invention was inserted into the duct and the amount of dirt staying behind in a duct when another duct cleaning tool not according to the invention was inserted into the duct was measured by an ATP swab test. ATP (adenosine triphosphate) is always present in animals, plants, microbes, etc. The ATP swap test measures the ATP so as to numerically grasp dirt or the like staying behind.

Example

A cleaning tool with elastic porous members made of sponge as shown in FIG. 1 was manufactured.

Comparative Example 1

A cleaning tool with a feather brush was prepared.

Comparative Example 2

A cleaning tool with a plastic brush harder than the aforementioned feather brush in Comparative Example 1 was prepared.

(Test Method)

1. Measurement of Base Value

Measuring sponge was washed, and a part of the sponge was cut. ATP adhering to the sponge was measured. A value obtained by this measurement will be used as a base value hereinafter.

2. Actual Measurement

Actual measurement was carried out in the following procedure.

(1) Fill a certain-length tube with human blood.

(2) Clean the tube with the cleaning tool according to each of Example and Comparative Examples 1 and 2 using alkali detergent together.

(3) Insert into the tube the measuring sponge, which was partially cut for measuring a base value.

(4) Measure ATP adhering to the measuring sponge after the insertion.

Further, ATP was measured by the same work as the aforementioned work, using the tube after lapse of 24 hours since the tube was filled with the human blood.

ATP was measured using "LuciPac Wide" (product name, Kikkoman Corporation) including ATP extraction reagent and luminescence reagent as reagents and using "Lumitester PD-10N" (product name, Kikkoman Corporation) as a measuring instrument. That is, the measuring sponge was soaked in a test tube to which the aforementioned ATP extraction reagent and the aforementioned luminescence reagent were added. This test tube was set in the measuring instrument "Lumitester PD-10N", and the amount of luminescence (RLU: Relative Light Unit) was measured. This amount of luminescence correlates with the amount of ATP adhering to the measuring sponge, that is, the amount of ATP staying behind in the tube. A smaller amount of luminescence means a smaller amount of ATP staying behind, that is, a higher cleaning effect.

For the measurement, a base value corresponding to the amount of ATP which had adhered to the measuring sponge itself initially was measured using a part of the measuring sponge by the aforementioned method. The base value was subtracted from an actually measured value measured by the aforementioned method, so as to obtain the amount of ATP staying behind in the tube accurately.

(Test Result)

The aforementioned test was performed using each cleaning tool according to Example, Comparative Example 1 and Comparative Example 2, so as to obtain an amount of luminescence (RLU) caused by ATP adhering to the measuring sponge individually. This result is shown in the following Table 1.

Numeric values in the following Table 1 designate the amounts of luminescence (RLU) respectively, meaning that the lower the value is, the higher the cleanliness is with less dirt. In addition, in Table 1, the "base value" designates the amount of luminescence (RLU) caused by ATP adhering to the measuring sponge itself, and the "actually measured value" designates the amount of luminescence (RLU) measured from the measuring sponge inserted after filling with blood and insertion of each cleaning tool.

TABLE 1

| | Just After Filling With Blood | | Lapse of 24 Hours After Filling With Blood | |
|---|---|---|---|---|
| | Base Value | Actually Measured Value | Base Value | Actually Measured Value |
| Example | 46 | 247 | 17 | 4214 |
| Comparative Example 1 | 6 | 300521 | 16 | 322009 |
| Comparative Example 2 | 81 | 16335 | 92 | 154859 |

(Unit: RLU)

As shown in Table 1, in the case where cleaning was carried out just after filling with blood, the amount of luminescence about 1,216.7 times as large as that in Example was measured in Comparative Example 1, and the amount of luminescence about 66.1 times as large as that in Example was measured in Comparative Example 2. It was proved that the cleaning efficiency in Example is extremely high.

Likewise, in the case where cleaning was carried out after 24 hours had passed since filling with blood, the amount of luminescence about 76.4 times as large as that in Example was measured in Comparative Example 1, and the amount of luminescence about 36.7 times as large as that in Example was measured in Comparative Example 2. Also in this case, it was proved that the cleaning efficiency in Example is extremely high.

Description of Reference Numerals and Signs

| | |
|---|---|
| 1, 1a, 1b, 1c, 1d, 1e, 1f, 1g | endoscopic duct cleaning tool (cleaning tool) |
| 10 | core wire |
| 20, 20b, 20c, 20d, 20e, 20f, 20g | elastic porous member |
| 21, 27, 29 | cut |
| 23, 28 | recess |
| 24 | groove |
| 30 | resin tube |
| 50 | endoscope |
| 53 | duct |

The invention claimed is:

1. An endoscopic duct cleaning tool which is inserted into a duct of an endoscope to clean the duct, comprising:
a core wire which includes a stranded wire;
a plurality of cylindrical elastic porous members which are disposed at certain intervals and at certain places in an axial direction of the core wire so as to directly cover outer circumferences of the core wire; and
resin tubes which cover outer circumferences of portions of the core wire which are not covered with the elastic porous members,
wherein ones of the elastic porous members or sets of the adjacently-disposed elastic porous members are disposed in plurality at the certain intervals,
wherein the resin tubes are formed:
to have an outer diameter larger than that of an inner diameter of the elastic porous members;
to be divided into
a frontmost end tube disposed at a frontmost end side of the frontmost elastic porous member,
an inter-porous-member tube disposed between the ones or sets of the elastic porous members and
a basemost end tube disposed at a basemost end side of the basemost elastic porous member; and to entirely cover the outer circumferences of the core wire except portions covered with the elastic porous member, and wherein at least the frontmost end tube and the basemost end tube are fixedly attached to the core wire.

2. The cleaning tool of claim 1,
wherein the elastic porous members are directly bonded to the core wire.

3. The cleaning tool of claim 1,
wherein the sets of the elastic porous members are disposed in plurality at the certain intervals and at the certain places in the outer circumference of the core wire.

4. The cleaning tool of claim 1,
wherein the frontmost end tube extends by a certain length from a frontmost end of the core wire.

5. The cleaning tool of claim 1,
wherein at least one kind of cuts, grooves and recesses is formed in an outer circumferential surface of each of the elastic porous members.

6. The cleaning tool of claim 5,
wherein the cuts are formed:
- to have a depth which extends from the outer circumferential surface of the elastic porous member but does not reach the core wire;
- to have an annular, spiral or arc shape extending in a circumferential direction of the elastic porous member; and
- to be arranged at certain intervals in the axial direction of the elastic porous member.

* * * * *